United States Patent [19]

Pashley et al.

[11] Patent Number: 5,360,880
[45] Date of Patent: Nov. 1, 1994

[54] POLYMERIZABLE PORPHYRINS

[75] Inventors: Richard M. Pashley, Aranda; Timothy J. Senden, Lyneham; Richard A. Morris, Grose Wold, all of Australia; James T. Guthrie, Kippax Leeds; Wei D. He, Leeds, both of United Kingdom

[73] Assignees: The Australian National University, Australian Capital Territory; The Acton and Memtec Ltd., New South Wales, both of Australia

[21] Appl. No.: 961,729
[22] PCT Filed: Jul. 5, 1991
[86] PCT No.: PCT/AU91/00298
§ 371 Date: Mar. 5, 1993
§ 102(e) Date: Mar. 5, 1993
[87] PCT Pub. No.: WO92/01007
PCT Pub. Date: Jan. 23, 1992

[30] Foreign Application Priority Data

Jul. 6, 1990 [AU] Australia ............... PK1083

[51] Int. Cl.$^5$ .............. C08F 2/00; C08F 226/06; C08F 216/34; C08F 220/10
[52] U.S. Cl. .................. 526/213; 526/216; 526/258; 526/315; 526/328.5; 525/298; 525/326.7; 525/328.7
[58] Field of Search ............... 526/258, 213, 216, 315, 526/328.5; 525/298, 326.7, 328.7; 548/420; 540/145

[56] References Cited

FOREIGN PATENT DOCUMENTS 63-238078 10/1988 Japan .

Primary Examiner—Joseph L. Schofer
Assistant Examiner—Wu C. Cheno
Attorney, Agent, or Firm—Sughrue, Mion, Zinn, Macpeak & Seas

[57] ABSTRACT

Polymerisable materials produced by the reaction of a pyrrole and an unsaturated or polymerisable aldehyde, preferably a beta-unsaturated aldehyde.

Polymers made from the above-described polymerisable material and copolymers formed from the said material and at least one other polymerisable monomer of a known type.

Such polymers and copolymers may be used for the production of films, coatings and other structures.

36 Claims, No Drawings

POLYMERIZABLE PORPHYRINS

This invention relates to polymerisable porphyrins and methods for their manufacture, polymers formed therefrom and use of such polymers as films and coatings.

We have found that the condensation of a beta-unsaturated aldehyde and a pyrrole can give rise to a monomeric product which contains a porphyrin bearing unsaturated substituents. This monomeric material then readily polymerises to produce polymeric product. Similar products can be produced using other unsaturated or polymerisable aldehydes According to the present invention there is provided a polymerisable material produced by the reaction of a pyrrole and an unsaturated or polymerisable aldehyde, preferably a beta-unsaturated aldehyde.

The pyrrole may be the unsubstituted pyrrole molecule itself, or it may bear substituents. Particulary preferred substituted pyrroles are those formed by addition to the pyrrole ring of acrylate or vinyl monomers. The preferred aldehydes are crotonaldehyde or acrolein.

The invention also includes polymers made from the above-described material and to films, coatings and other structures made from such a polymer.

The invention also extends to copolymers formed from the above-mentioned polymerisable material and at least one other polymerisable monomer of a known type. Examples of such co-monomers are vinyl monomers, such as styrene, and acrylic acid or acrylate monomers, such as acrylic acid itself or methyl methacrylate. The polymers of the invention will also initiate the radical polymerisation of such monomers.

The invention further extends to substrates having a coating of the above-mentioned polymers.

The polymerisable materials of this invention may be produced by the reaction of the major components, the pyrrole and the aldehyde, in the presence of an acid catalyst.

The acid catalyst may be an organic acid, such as acetic or propionic acid, or an acid anhydride, such as phthalic anhydride.

To illustrate the process of the invention by way of example, a dark viscous paint can be easily produced by mixing pyrrole, crotonaldehyde and propionic acid. If the mixture is allowed to stand at room temperature for a period of time (the induction time), it rapidly increases in viscosity and can then be painted onto some suitable substrate. The resultant black coating sets rapidly, is chemically inert and adheres strongly to glass and metal substrates.

The induction time (prior to the rapid polymerisation stage) can be varied from a few minutes to several hours by using different acids and/or varying the acid concentration. It is likely that during the induction period the tetracrotonyl porphyrin (TCP) (or tetraacrolein porphyrin (TAP)) molecule is formed, which when present at significant concentrations initiates further, rapid polymerisation of the aldehyde and pyrrole.

The reaction normally proceeds well at room temperature, but in some circumstances it may be advantageous to work at or near the thermodynamically favoured temperature of 55° C.

The chemical composition of the resulting polymer is difficult to obtain but most likely consists of linear chains in a porphyrin star polymer matrix.

Due to the strongly adherent nature of the polymers of the invention, they can be used in areas of reasonably high mechanical/fluid work. The electronic nature of the ring nitrogens allows for a high degree of binding to metals ions. With the metal ion in place gases may also be selectively bound (c.f. haem). The monodispersity of pore size is also a noted advantage of this molecule. Taking the above attributes together, the polymers of the invention may find applications in the following areas:

Ion selective electrodes. Standard inert (e.g. glass) electrodes may be converted to ion selective detectors by coating with a thin film of the polymeric porphyrin. In addition, binding iron (II) to the porphyrin may also allow detection of the oxygen content of water.

Copolymers. Monomeric styrene or methyl methacrylate may be initiated by the porphyrin as it polymerises. The resultant copolymer may be used as a porous or non-porous coating material.

Water purification; extraction of heavy metal ions. The observation that these porphyrin polymers will combine with divalent heavy metal ions, also leads to the use of the polymers in the purification of water contaminated with such cations. Initial observations indicate that the porphyrin binds and polymerises to produce an insoluble, heavy polymer which readily settles out of aqueous solution thereby removing the heavy metal ions.

Metal finishing. Coatings for e.g. the automotive, white goods and marine industries.

For coating applications, control of rheological characteristics is important and to this end, it may be desirable or necessary to modify the polymeric materials of the present invention, for example, by the addition of known coating assemblies.

Examination of the reaction system pyrrole/crotonaldehyde/propionic acid, shows that once the reaction is initiated, the three-dimensional, highly crosslinked structure develops rapidly resulting in a poorly (rheologically) characterised polymeric mixture. It is important, therefore, to be able to control the polymerisation reaction and thereby to allow the transition from liquid to solid state to occur more uniformly.

To successfully incorporate the porphyrin polymers of the invention into coatings, for example for use with metals, the crosslinking reaction should be terminated when it reaches a certain stage. One approach to this involves either (a) terminating the reaction by addition of ammonia ($NH_3$) to the reaction system, or (b) protecting or blocking the active >CHOH groups which are formed during the polymerisation reaction, thus stabilising the groups and preventing or reducing their participation in further crosslinking. Such protection or blocking will generally involve forming derivatives of the OH groups, for example ether or ester groups. Among the reagents which can be used for this purpose are polymerisable monomers, oligomers or other polymer precursors which possess appropriate reactive groups. Oligomer types which contain such groups capable of protecting the >CHOH groups include:
(i) Melamine based oligomers
(ii) Epoxy oligomers
(iii) Polyurethane oligomers or
(iv) Alkyd resin precursors.

Preferred oligomer types are the alkyd resin precursors, such as acrylicmelamine, melamine-alkyd or simple alkyd formulations, all of which contain residual —OH groups capable of reacting with >CHOH, leading to etherification. Examples include castor oil base alkyds, soya bean oil alkyds, rosin esters, —OH rich esters and COOH rich esters (rosin precursors), —OH deficient and —COOH deficient resins.

Another approach to controlling the properties of the polymers of the invention is to modify the pyrrole starting material before or during the polymerisation reaction. Particularly useful results can be obtained by pre-reacting (unsubstituted) pyrrole with a vinyl or acrylic monomer before reaction with the aldehyde, or by adding such a monomer to the pyrrole/aldehyde reaction mixture. In the case of an acrylic monomer, for example, it is believed that substitution of the acrylate moiety occurs at the 2-position of the pyrrole ring, to give products of the form

or

where Py=2-pyrrolyl and R=hydrogen or an alkyl group

Butyl acrylate is particularly useful in this regard and the presence of the ester groups in the final product generally confers improved properties, such as resilience and flow characteristics.

The pyrrole-crotonaldehyde system may thus benefit from being part of a formulation designed to give effective coatings which will flow, transfer, wet, film-form, adhere and dry while maintaining its integrity and providing the required protection to a substrate.

The pyrrole-crotonaldehyde polymers may be incorporated into alkyd formulations and in acrylic formulations which by their nature possess reactivity through both —OH groups and —COOH groups. As explained above the pyrrole-crotonaldehyde reaction results in the formation of secondary —OH groups. By etherification of these groups in systems with alkyd resin prepolymers, more effective coatings can be obtained.

The invention is further described and illustrated by reference to the following Examples. It should be noted that these Examples should not be construed as limiting the invention in any way.

EXAMPLE 1

Preparation of Polymer

Crotonaldehyde (0.7 g) pyrrole (0.67 g) and 5 ml propionic acid were mixed together at room temperature and allowed to stand until the blue colour of porphyrin was visible. This was extracted into 5 ml of chloroform. The chloroform extract was then washed three times with 5 ml of water (or until the aqueous phase was neutral). The chloroform solution was then dropped gently onto the surface of a water trough (e.g. a Langmuir trough) until uniform spreading of a thin film occurred.

The thin layer was then allowed to polymerise. This solid two-dimensional layer could then be coated onto a wide range of solids with generally strong adhesion.

EXAMPLE 2

Preparation of Coated Electrodes

The Langmuir-Blodgett polymerised film of Example 1 was coated onto an electrochemically inert electrode surface (Selectrode, Radiometer). Prior to coating the, electrode, when combined with a reference Calomel electrode (Radiometer) and connected to an electrometer (Keithley 614), showed no response to $FeCl_2$ solutions over the concentration range $10^{-5}$ to $10^{-1}$ M. After coating, the electrode response observed was about 30 mv/decade change in $Fe^{2+}$ concentration. This is very close to the theoretical limit given by the Nernst equation. The layer clearly gives electrochemical activity to the inert electrode.

Other ions which are already known to combine with porphyrin molecules e.g. $Mg^{2+}$, $Zn^{2+}$, $Cd^{2+}$ may be similar, whereas, monovalent cations do generally not interfere with the electrode. Anions are also not expected to affect the response of the electrode.

EXAMPLE 3

Metal Ion Removal from Aqueous Solution 0.67 g of pyrrole was dissolved in 10 ml of acid solution (pH=4) and then 0.7 g crotonaldehyde was added. This mixture was then added to 0.1M $FeCl_2$ (50 ml) and allowed to stand at room temperature for 48 hours after initial stirring. The mixture was then centrifuged to remove the black polymer. The resultant supernatant solution had a $Fe^{2+}$ content of less than $10^{-5}$M.

EXAMPLE 4

Formation of a Porphyrin Paint

A dark viscous paint was produced by mixing pyrrole, crotonaldehyde and propionic acid, in the proportions shown in the table below. The mixture was allowed to stand at room temperature and after a period of time (the induction time), it rapidly increased in viscosity and could then be painted onto a substrate. The resultant black coating set rapidly, and was found to be chemically inert and strongly adherent to glass and metal substrates.

Addition of about 2% polyethylene oxide (MW about $4 \times 10^6$) produced a higher viscosity mixture which was more easily applied or coated during the induction period.

The induction time prior to the rapid polymerisation stage could be varied over a few minutes to several hours using different acids and/or varying the acid concentration. Examples of the effect of acid on polymerisation time in the presence of polyethylene oxide viscosifier are given in the table below.

| pyrrole/crotonaldehyde 1:1 (by wt) polyethylene oxide 2% (by wt) | |
|---|---|
| propionic acid/crotonaldehyde (by wt) wt) | time (mins) to polymer setting |
| 0.3 | 135 |
| 0.6 | 68 |
| 1.0 | 45 |
| 1.5 | 35 |

The use of acetic acid instead of propionic causes the polymer to set within about 5 mins. Addition of preformed polymer to the reaction mixture also reduces the induction time.

The resulting polymer inhibited corrosion of stainless steel rings (315) when the rings coated with the polymer were placed in 0.9% saline (NaCl) solutions for 14 days at room temperature and 60° C.

EXAMPLE 5

Production of a Modified Polymer using Butyl Acrylate

A polymer was produced using the following starting materials.

| materials | percentage | weight (g) |
|---|---|---|
| pyrrole | 26.99 | 67 |
| crotonaldehyde | 39.48 | 98 |
| butyl acrylate | 30.96 | 76.8 |
| propionic acid | 2.58 | 6.4 |
| ammonia (25-28%) |  | As required |
| dimethylbenzene (solvent) |  | As required |

The pyrrole, butyl acrylate and propionic acid were mixed and heated at 45°–50° C. for 1–4 hours and the crotonaldehyde was then added drop by drop over a period of 20 minutes to 5 hours. The ammonia was then added to give a pH of 6–7.

The resulting porphyrin derivative was then washed with dimethyl benzene to give a semi-finished product, which can then be subjected to further etherification and/or esterification, e.g. using alkyd resin and/or other prepolymers. The nature of such reaction will depend on the chemical composition of the chosen alkyd, i.e. whether it is rich in —OH or —COOH.

For example, the porphyrin derivative, prepared as above can be included in coating assemblies by combining a commercial resin assembly, the porphyrin derivative and phthalic anhydride and heating the mixture at 100°–110° C. and pH 4–4.5, followed by esterification and/or etherification to give a final coating composition.

The actual formulation will vary with the resin type, and the acid number/—OH number of the resin.

EXAMPLE 6

Modifications to the Pyrrole/Crotonaldehyde System

The rate of reaction is closely related to the equivalent ratio of the reactants. Bearing in mind the economic factors, it is preferred to use crotonaldehyde as the excess reagent because (i) it is cheaper than pyrrole and (ii) it can substitute carbons in positions 2, 3, 4 and 5 of the pyrrole ring. The substituted pyrrole is slower in crosslinking than unsubstituted pyrrole. Thus, the overall reaction is more stable and thus more easily controlled.

The following data illustrates this aspect.

| Pyrrole to crotonaldehyde ratio | Time for porphyrin ring formation (min) | Time for gelation (min) |
|---|---|---|
| 1:1 | 120 | 128 |
| 1:1.4 | 74 | 254 |
| 1:2 | 480 | 690 |
| 1:3 | 540 | 765 |
| 1:4 | 780 | 1070 |

It is clear from the above results that 1:1.4 is the optimum pyrrole to crotonaldehyde ratio. With this composition, porphyrin formation took 74 minutes and gelation occurred after the reaction had progressed for 254 minutes. The time between porphyrin formation and gelation, which is 180 minutes, is long enough to allow other modifications to the system to take place.

EXAMPLE 7

Effect of Catalyst System

Propionic acid, when used as catalyst, prevents further reactions, such as blocking of >CHOH groups, from taking place and must therefore be removed from the system before the >CHOH group blocking reaction(s) can take place. It was found that when phthalic anhydride was used as the catalyst for the >CHOH blocking reaction, it can also effectively catalyse the crosslinking of pyrrole and crotonaldehyde, and has the effect of making the reaction easier to control. Thus, using a 1:1.4 mixture of pyrrole and crotonaldehyde containing 0.25% phthalic anhydride resulted in (modified) porphyrin formation in 50 minutes and gelation at 960 minutes.

Therefore, phthalic anhydride may replace propionic acid as the catalyst in porphyrin formation, and probably acts as both a reagent and a catalyst.

EXAMPLE 8

Blockage of >CHOH Active Groups present in the Pyrrole-Crotonaldehyde Intermediate Prepolymer To avoid gelation of the system, it is necessary to block >CHOH groups in the system before complete crosslinking occurs. As a model for an alkyd resin which would be rich in hydroxyl groups, butanol was used as the blocking reagent. The reaction mechanism is essentially as follows:

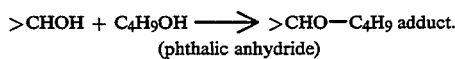

$$>CHOH + C_4H_9OH \longrightarrow >CHO-C_4H_9 \text{ adduct.}$$
(phthalic anhydride)

Reasonably good coating materials were obtained after the reaction was allowed to proceed for 1–2 hours at 110° to 120° C.

EXAMPLE 9

Pyrrole Modification-Butyl Acrylate Addition

A 1:0.6 mixture of pyrrole and butyl acrylate containing phthalic anhydride (0.25%) as catalyst was allowed to react at 20° C. for 1 hour. The intermediate product thus obtained was then mixed with crotonaldehyde in the ratio 1:1.4 and the mixture allowed to react, again at 20° C. for 1 hour, to produce a dark blue polymer(I).

A portion of (I) was mixed with butanol (25%) and heated for 2 hours at 110° C. This composition can then be used, either on its own or it can be incorporated into other formulations, e.g. with alkyds.

EXAMPLE 10

Formulations (A) Polymer (I)+Alkyd Systems

The following formulations were prepared using the polymer (I) from the previous example:

| | |
|---|---|
| (a) 25% of (I) with 75% Vilkyd 141 × 55 | (II) |
| (b) 25% of (I) with 75% Vilkyd 161 × 55 | (III) |

In both instances, a dark blue primary coating is obtained which can be used as a dip or brush coating system.

Vilkyd 141×55 and 161×55 are alkyd resin systems. The 141×55 is a phenolic modified, chain stopped alkyd, whereas the 161×55 is a rosin-modified linseed/linoleic alkyd. Both are manufactured by Vanish Industries Ltd., Bolton, Lancs., (U.K.).

The addition of butyl acrylate to the pyrrole causes a reduction in the rate of curing in the pyrrole/crotonaldehyde system, although not an increase in the induction period, thereby giving greater control. A more rapid, controlled reaction can be achieved by heating.

The added butyl acrylate also provides the coating with greater adhesion, flexibility and toughness, even in very thin films and even without blending with other resin/film forming assemblies. Adhesion is also markedly improved.

The butyl acrylate modified porphyrin system coupled with the Vilkyd resin gives excellent compatibility. The level of adhesion of the systems to metals follows the order (I)>(II)≈(III). However, the coating adhesion/flexibility/toughness of the films is excellent in all cases.

In a variation of the procedure given in Example 8, The pyrrole was first reacted with the crotonaldehyde, in the presence of phthalic anhydride, for 4.5 hours to give the porphyrin polymer. The latter was then reacted with butanol as before to give the final product (IV).

Using 40% of (IV) and 60% Vilkyd 161×55, the formulation was developed and coatings cast. A dry, blue coating was obtained after 15 minutes.

With 40% of (IV) and 60% of Vilkyd 141×55, the coating was cast and gave a dry, blue film in 11 minutes. This coating was easily achieved to give excellent flexibility in dense coatings.

(B) Alternative acrylate assemblies using an epoxy acrylate

Pyrrole (27%), crotonaldehyde (40%) and an epoxidised soya bean oil acrylate (Ebecryl 860-UCB Belgium) (32.75%) were reacted together in the presence of phthalic anhydride (0.25%) at room temperature. This formulation was used as a coating by applying it to a substrate and irradiating it with UV light (254 nm) for 30 minutes.

A second alternative acrylate assembly involved the use of borneyl acrylate, which is an acrylated pine extract monomer capable of providing great flexibility to UV curable formulations whilst meeting current safety requirements. The borneyl acrylate (32.75%) was mixed with pyrrole (27%) and heated at 21° C. in the presence of propionic acid (0.25%) for 40 minutes, after which crotonaldehyde (40%) was added. The UV polymerisable system was obtained after 7 hours. The addition of butanol as a blocking agent gives a good coating system which can be used in conventional curing.

EXAMPLE 11

Testing of Formulations

The following formulations were used:
1. A formulation based on the polymer of Example 4, using a crotonaldehyde:pyrrole ratio of 1:1. The coating, on application, was allowed to dry in air over five days.
2. A formulation based on a polymer containing the optimised ratio of pyrrole:crotonaldehyde (1:1.4). This polymer comprises 25% of the total formulation. Vilkyd 161×55 (Vanish Industries Ltd) 50% and butanol 25% are the other components.
3. A formulation containing 25% of the product produced by reacting pyrrole, crotonaldehyde and butyl acrylate (1:1.4:0.6) at room temperature. Vilkyd 161×55 (50%) and butanol (25%) make up the balance of the formulation.
4. A formulation containing 25% of the product produced by reacting pyrrole, crotonaldehyde and butyl acrylate (1:1.4:0.6) at 55° C., Vilkyd 161×55 (50%) and butanol (25%).

Corrosion Studies

Two metallic substrates were used. For simplicity, standard mild steel 4" (100 mm) nails of approximately 3/16" (4.8 mm) diameter were used. In addition, mild steel wire pins were used. These were 2½" (63.5 mm) in length and 1/16" (1.6 mm) in diameter.

Dip coating was utilised throughout and the coating allowed to air-dry over a constant time period (5 days) to ensure complete cure of all of the formulations.

RESULTS

Test Solution-Assembly and Procedure

The test solutions, as shown in Table 1, represent a range of conditions of exposure for the coated nails/pins over 5 days of exposure.

x denotes the development of some rust after 5 days of exposure to the assembled corrosive solutions however, still superior to the controls (uncoated).

√ denotes that no evidence of corrosion whatsoever is seen.

Table 2 gives data for longer term exposure of the coated samples at the elevated temperature of 45° C.

Coatings 5 and 6 are the same as 4. However, the coated samples were exposed to the corrosive solution for 5 days after the coating had been allowed to dry for 17 days (coating 6) and 23 days (coating 5).

From Tables 1 and 2, it is easy to see which are the effective formulations. Table 2 clearly shows that the level of corrosion protection is influenced by the drying conditions under which the coating is developed. It was also noted that the scratch resistance increases as the curing time increases. Butyl acrylate inclusion in formulations is a positive factor to corrosion prevention.

TABLE 1

| | TEST SOLUTIONS (*g/kg water) | | | | | |
|---|---|---|---|---|---|---|
| SAM-<br>PLE NO | $Na^+$* | 10.615 | 13.23 | 11.765 | 10.615 | 10.615 |
| | $Cl^-$* | 18.89 | 19.38 | 16.384 | 16.384 | 16.384 |
| | $SO_4^{2-}$* | 2.65 | 2.65 | | | |
| | $H^+$* | 0.1226 | 0.226 | | | |
| | $OH^-$* | | | 0.85 | | |
| | Temp °C. | 20 | 20 | 20 | 20 | 45 |
| | pH | 2 | 4 | 13 | 7 | 7 |
| 1 | | x | x | x | x | x |
| 2 | | x | √ | x | x | x |
| 3 | | √ | √ | x | x | x |
| 4 | | √ | √ | √ | x | x |

TABLE 2

| SAMPLE NO. | $Na^+$ 10.65 g/kg water;<br>$Cl^-$ 16.384 g/kg water;<br>pH 7; 45° C. | Resistance to Scratch |
|---|---|---|
| 4 | x | Easy to scratch off (rusty) |
| 5 | √ | Difficult to scratch off |
| 6 | √ | Easy to scratch off |

EXAMPLE 12

Coating Systems

Coating systems based on the following compositions were prepared:

| System A: | |
|---|---|
| Porphyrin prepolymer[1] | 26% |
| Resin 4835[2] | 34% |
| Butanol | 26% |
| Acrylic acid | 6% |
| Xylene | 8% |
| System B: | |
| Porphyrin prepolymer[1] | 46% |
| Butanol | 50% |
| Acrylic acid | 4% |

Notes:
[1]Product produced by reacting pyrrole, crotonaldehyde and butyl acrylate (1:1.4:0.6) at room temperature.
[2]Resin 4835 (UCB) is composed of 90% of an acrylated urethane resin and 10% of tetraethyleneglycol diacrylate.

Mild steel substrate samples (as described in Example 11) were coated with the above systems and cured at room temperature for from 20 seconds to 5 minutes. The coated samples were tested for their resistance to acids, bases, saline solutions, organic solvents and elevated temperatures (baking). The test and results are set out in Tables 3 to 6 below. The results show that the incorporation of acrylic acid and the urethane acrylate give marked improvements in the solvent and corrosion resistance of the porphyrin polymers.

TABLE 3

Anticorrosion Properties in Saline Solutions

| System | Observation (125° C., 2.7% NaCl, pH 7) |
|---|---|
| A. | 265 hours, no rust observed, hard coating.[1] |
| B. | 48 hours, some rust observed, hard coating. |

[1]Wrinkling of the coating was observed in the part not immersed in the solution.

TABLE 4

Solvent Resistance Studies

| System | Observation (In dimethyl benzene) |
|---|---|
| A. | 265 hours, no coating removal observed, hard coating with tiny pores. |
| B. | 265 hours, no coating removal observed, hard coating throughout. |

| System | Observation (In cyclohexanone) |
|---|---|
| A. | 2 hours, relative ease of coating removal[2] |
| B. | 265 hours, no coating removal observed, hard coating throughout. |

[2]Cyclohexanone is reactive to the —NH—COO— group, therefore dissolves the coating.

TABLE 5

Thermal Stability

| System | Observation (Baked at 125° C.) |
|---|---|
| A. | 64 hours, hard coating, no damage observed. |
| B. | 35 hours, hard and brittle coating, cracks observed |

TABLE 6

Anticorrosion Properties of System A in Various Saline Assemblies

| Corrosion System | Observation (Exposed for 265 hours) |
|---|---|
| 2.7% NaCl, pH2 | No rust observed, hard coating |
| 2.7% NaCl, pH4 | No rust observed, hard coating |
| 2.7% NaCl, pH7 | No rust observed, hard coating |

TABLE 6-continued

Anticorrosion Properties of System A in Various Saline Assemblies

| Corrosion System | Observation (Exposed for 265 hours) |
|---|---|
| 2.7% NaCl, pH13 | No rust observed, hard coating |

EXAMPLE 13

Comparison with Commercial Coating Formulations.

Studies similar to those described in Example 12, were conducted on the commercial formulations listed below and formulations in accordance with this invention.

| Code | Sample |
|---|---|
| 1. | "Homework" Black Bitumen (Kalon Ltd, Huddersfield Road, Batley, WF17, 2XA, U.K.) |
| 2. | Finnegans Hammerite Hammered Motel Finish (Black) (Hunting Speciality Products, P.O. Box 67, Leeds LS1 1LS.) |
| 3. | Hammerite Hammered Metal, Finish (Red) (Hunting Speciality Products.) |
| 4. | Comma Stop Rust (Comma, Gravesend, Kent.) |
| 5. | System A (Example 12) Thermally cured at 125° C. |
| 6. | System B (Example 12). Thermally cured at 125° C. |

TABLE 7

| Code | 2.7% NaCl | pH2 Room Temperature |
|---|---|---|
| 1 | 2 days | No damage, soft coating. Non-resistant to scratch. |
| 2 | 2 days | No damage, soft coating. Non-resistant to scratch. |
| 3 | 2 days | No damage, soft coating. Non-resistant to scratch. |
| 4 | 2 days | No damage, coating hard. |
| 5 | 24 days | No damage, coating hard. |

TABLE 8

| Code | 2.7% NaCl | pH4 Room Temperature |
|---|---|---|
| 1 | 2 days | No damage, soft coating. Non-resistant to scratch. |
| 2 | 2 days | No damage, soft coating. Non-resistant to scratch. |
| 3 | 2 days | No damage, soft coating. Non-resistant to scratch. |
| 4 | 2 days | No damage, coating hard. |
| 5 | 24 days | No damage, coating hard. |

TABLE 9

| Code | 2.7% NaCl | pH7 Room Temperature |
|---|---|---|
| 1 | 2 days | Some coating falls off the metal surface. |
| 2 | 2 days | No damage. Non-resistant to scratch. |
| 3 | 2 days | Some rust observed. |
| 4 | 2 days | Serious cracks observed. |
| 5 | 24 days | No damage, coating hard. |

TABLE 10

| Code | 2.7% NaCl | pH13 Room Temperature |
|---|---|---|
| 1 | 2 days | Some coating falls off the metal surface. |
| 2 | 2 days | No damage. Non-resistant to scratch. |
| 3 | 2 days | No damage, coating hard. |
| 4 | 2 days | Rusty. |
| 5 | 24 days | No damage, coating hard. |

TABLE 11

| Code | 2.7% NaCl | pH7 Room Temperature |
|---|---|---|
| 1 | 1 hr | Coating cracks |
|   | 2 days | Rusty, Serious coating cracks |
| 2 | 2 hrs | Coating cracks |
|   | 2 days | Rusty, Serious coating cracks |
| 3 | 4 hrs | Coating softened |
|   | 2 days | Rusty, Serious coating cracks |
| 4 | 1 hr | Coating softened |
|   | 2 days | Rusty, Serious coating cracks |
| 5 | 24 days | Coating hard |

TABLE 12

| Code | Cyclohexanone | Room Temperature |
|---|---|---|
| 1 | 2 min | Coating cracks |
|   | 30 min | All coating falls off the metal surface |
| 2 | 3 min | Some coating cracks |
|   | 15 min | Serious coating cracks |
| 3 | 5 min | Some coating cracks |
|   | 30 min | Serious coating cracks |
| 4 | 10 min | Some coating cracks |
|   | 30 min | Serious coating cracks |
| 6 | 25 days | No damage, coating hard |

TABLE 13

| Code | Dimethylbenzene | Room Temperature |
|---|---|---|
| 1 | 1 min | Some coating cracks |
|   | 30 min | All coating falls off the metal surface |
| 2 | 5 min | Some coating cracks |
|   | 30 min | Serious coating cracks |
| 3 | 5 min | Some coating cracks |
|   | 30 min | Serious coating cracks |
| 4 | 8 min | Some coating cracks |
|   | 30 min | Serious coating cracks |
| 5 | 25 days | Some tiny pores observed |
| 6 | 25 days | No damage, coating hard |

We claim:

1. The polymerizable material characterized in that it comprises the reaction product of a pyrrole and an unsaturated polymerizable aldehyde.

2. The polymerizable material as claimed in claim 1, characterized in that the aldehyde is a beta-unsaturated aldehyde.

3. The polymerizable material as claimed in claim 2, characterized in that the aldehyde is crotonaldehyde or acrolein.

4. A process for preparing a polymerizable material, characterized in that a pyrrole and an unsaturated polymerizable aldehyde are reacted in the presence of an acid catalyst.

5. The process as claimed in claim 4, characterized in that the acid catalyst is an organic acid or acid anhydride.

6. The process as claimed in claim 4, characterized in that the acid catalyst is acetic acid, propionic acid or phthalic anhydride.

7. The process as claimed in any one of claims 4 to 6, characterized in that the reaction is terminated when the desired state of crosslinking has been reached by addition of ammonia.

8. The process as claimed in any one of claims 4 to 6, characterized in that the reaction is terminated when the desired state of crosslinking reached by addition of a reagent capable of protecting or blocking >CHOH groups.

9. The process as claimed in claim 8, characterized in that the reagent is a primary alcohol.

10. The process as claimed in claim 9, characterized in that the reagent is n-butanol.

11. The process as claimed in claim 8, characterized in that the reagent is an oligomer.

12. The process as claimed in claim 11, characterized in that the oligomer is an alkyd resin precursor.

13. The process as claimed in any one of claims 4 to 6, characterized in that the pyrrole is modified before or during the reaction by addition of a vinyl or acrylic monomer to the reaction mixture.

14. The process as claimed in claim 13, characterized in that the acrylic monomer is butyl acrylate.

15. A polymeric material, characterized in that it is derived from a polymerizable material comprising the reaction product of a pyrrole and an unsaturated polymerizable aldehyde.

16. The polymeric material as claimed in any one of claims 15, 24 or 25; characterized in that it is a copolymer derived from the polymerizable material claimed in any one of said claims 15, 24 or 25, and at least one other polymerizable monomer.

17. A polymeric formulation characterized in that it comprises a polymeric material as claimed in claim 15, and one or more of the following:
   a) an alkyd system;
   b) an acrylate system;
   c) a primary alcohol.

18. A membrane, characterized in that it comprises a polymeric material as claimed in any one of claims 15, 24 or 25.

19. A coated substrate, characterized in that the coating comprises a polymeric material as claimed in any one of claims 15, 24 or 25.

20. The process as claimed in claim 7, characterized in that the pyrrole is modified before or during the reaction by addition of a vinyl or acrylic monomer to the reaction mixture.

21. The process as claimed in claim 20, characterized in that the acrylic monomer is butyl acrylate.

22. The process as claimed in claim 8, characterized in that the pyrrole is modified before or during the reaction by addition of a vinyl or acrylic monomer to the reaction mixture.

23. The process as claimed in claim 22, characterized in that the acrylic monomer is butyl acrylate.

24. The polymeric material as claimed in claim 15, characterized in that the aldehyde is beta-unsaturated aldehyde.

25. The polymerizable material as claimed in claim 24, characterized in that the aldehyde is crotonaldehyde or acrolein.

26. A polymeric formulation characterized in that it comprises a polymeric material as claimed in claim 16, and one or more of the following:
   a) an alkyd system;
   b) an acrylate system;
   c) a primary alcohol.

27. A membrane, characterized in that it comprises a polymeric material as claimed in claim 16.

28. A membrane, characterized in that it comprises a polymeric material as claimed in claim 17.

29. A membrane, characterized in that it comprises a polymeric material as claimed in claim 26.

30. A coated substrate, characterized in that the coating comprises a polymeric material as claimed in claim 16.

31. A coated substrate, characterized in that the coating comprises a polymeric material as claimed in claim 17.

32. A coated substrate, characterized in that the coating comprises a polymeric material as claimed in claim 26.

33. The process as claimed in claim 9, characterized in that the pyrrole is modified before or during the reaction by addition of a vinyl or acrylic monomer to the reaction mixture.

34. The process as claimed in claim 10, characterized in that the pyrrole is modified before or during the reaction by addition of a vinyl or acrylic monomer to the reaction mixture.

35. The process as claimed in claim 11, characterized in that the pyrrole is modified before or during the reaction by addition of a vinyl or acrylic monomer to the reaction mixture.

36. The process as claimed in claim 12, characterized in that the pyrrole is modified before or during the reaction by addition of a vinyl or acrylic monomer to the reaction mixture.

* * * * *